United States Patent [19]

Begemann

[11] Patent Number: 5,312,447
[45] Date of Patent: May 17, 1994

[54] PACEMAKER WITH IMPROVED INHIBIT AND TRIGGER CONTROL

[75] Inventor: Malcolm J. S. Begemann, Velp, Netherlands

[73] Assignee: Vitatron Medical, B.V., Netherlands

[21] Appl. No.: 950,479

[22] Filed: Sep. 24, 1992

[51] Int. Cl.$^5$ ............................................. A61N 1/362
[52] U.S. Cl. ......................................................... 607/9
[58] Field of Search ................................. 128/419 PG

[56] References Cited

U.S. PATENT DOCUMENTS

| | | | |
|---|---|---|---|
| 3,523,539 | 8/1970 | Lavezzo et al. | 128/419 PG |
| 3,985,142 | 10/1976 | Wickham | 128/419 PG |
| 4,023,121 | 5/1977 | Alley, III | 128/419 PG |
| 4,148,320 | 4/1979 | Ohara | 128/419 PG |
| 4,202,341 | 5/1980 | Blaser | 128/419 PG |
| 4,335,727 | 6/1982 | McPherson | 128/419 PG |
| 4,513,743 | 4/1985 | van Arragon et al. | 128/419 PG |
| 4,788,980 | 12/1988 | Mann et al. | 128/419 PG |
| 4,856,522 | 8/1989 | Hansen | 128/419 PG |
| 5,097,832 | 3/1992 | Buchanan | 128/419 PG |
| 5,144,950 | 9/1992 | Stoop et al. | 128/419 PG |

OTHER PUBLICATIONS

Tech Note, Medtronic Technical Service Department, Issue No. 91-3, Oct. 29, 1991.

Primary Examiner—William E. Kamm
Attorney, Agent, or Firm—Woodcock Washburn Kurtz Mackiewicz & Norris

[57] ABSTRACT

A pacemaker for providing optimized inhibit and trigger responses, operating in a VVD or AAD mode. For each pacemaker cycle, the pacemaker is controlled to time out a refractory interval, an inhibit interval or range following a refractory interval, and a trigger interval or range which follows the inhibit interval and ends at the time out of the scheduled escape interval. A signal sensed during the inhibit range results in no pace pulse delivery, the pacemaker goes to the trigger mode and extends the escape interval. Any signal thereafter sensed before the time out of the extended escape interval results in delivery of a trigger pulse and restarting of a new pacemaker cycle. If no signal is sensed during the inhibit range, any signal sensed during the trigger range results in generation of a trigger pulse and the start of a new pacemaker cycle. The overall result is that noise or other signals which occur within the inhibit range are inhibited without a trigger, with only a small extension of the escape interval so that pacing rate is not greatly affected. Any signal sensed in the trigger range results in delivery of a trigger pulse. The result is an optimized combination of inhibition and triggering which ensures pacing in the presence of any noise that is sensed with relatively minimized sacrifice in rate change and battery energy depletion.

17 Claims, 3 Drawing Sheets

PACEMAKER WITH IMPROVED INHIBIT AND TRIGGER CONTROL

BACKGROUND OF THE INVENTION

1. Field of the Invention

This invention relates to implantable cardiac pacemakers and, more particularly, an AAD or VVD mode pacemaker adapted to inhibit or trigger depending upon the timing of each sensed signal.

2. Description of the Prior Art

Implantable pacemakers have developed to the point where a wide variety of different pacemaker modes and functions are available. Relatively early in the development of implantable cardiac pacemakers, it was recognized that it was desirable to permit an underlying natural cardiac beat to occur without pacemaker interference. Thus, pacemakers were developed to function in the inhibit, or demand mode, wherein if a natural heartbeat is detected within the pacemaker escape interval, the pacemaker timing is reset and no pace pulse is delivered. The inhibited mode thus saves battery energy and prevents competition of a delivered pace pulse with a natural cardiac rhythm. However, it was recognized that the demand pacemaker could be vulnerable to false sensing, i.e., it could inhibit upon the sensing of noise or other artifacts instead of a true natural beat. In such an event, the pacemaker would fail to deliver a timely stimulus, with detrimental consequences. An answer to this possibility is to operate in the triggered mode, whereby a sensed event triggers the pacemaker to deliver a pace pulse immediately following the sensed event. In this way, the pacemaker ensures that it is not inhibited due to a false sensed event, and does not compete with the underlying heartbeat. Of course, the trigger mode carries the liability of expending extra battery energy due to delivering heartbeats when there is no need to do so. A ventricular pacemaker which operates in the inhibit mode is classified as VVI; a ventricular pacemaker which operates in the trigger mode classified as VVT; and a ventricular pacemaker which can operate in either mode is classified as VVD. Similarly, an atrial pacemaker may be either AAI, AAT, or AAD.

Most present day pacemakers operate in the inhibit mode. Improvements in amplifier filtering and techniques for recognizing the natural heartbeat waveform to the exclusion of noise and extraneous signals normally permit a high degree of reliability in sensing only the true heartbeat signals. However, present day circuitry still does not provide 100% protection against low rate noise, such as emanates from the patient's muscle. Normally, everything below about 13 Hz is sensed in pacemakers, such that there remains a need to deal with the possibility of low frequency noise sensing. For this reason, there exists a need for an improved pacemaker design which can provide an optimum VVD or AAD mode of operation.

SUMMARY OF THE INVENTION

It is an object of this invention to provide an improved inhibit/trigger pacemaker, e.g., a pacemaker which can operate in an AAD or VVD mode. The improved pacemaker provides for inhibition of every other sensed signal under circumstances where the sensed signals manifest a relatively high rate; and triggers following sensed signals which precede the expected natural beat by only a predetermined small time interval, whereby triggering on noise does not result in too quick a resultant pacing rate.

In accordance with the above object, there is provided a pacemaker and a method of operating same which defines an inhibit time range following each last event, the pacemaker responding to any sensed event within the inhibit time range by extending the escape interval to a longer interval without delivering a trigger pace pulse. A trigger time range is also defined between the end of the inhibit range and the end of the normally scheduled escape interval, the pacemaker being controlled to generate a trigger pulse in response to any signal sensed during the trigger range. Additionally, following a sensed event in the inhibit range, the pacemaker is also in a trigger mode until the time out of the extended escape interval. By making the extended escape interval substantially twice the time of the end of the inhibit range, sensed signals which occur in the inhibit range are triggered at a 1:2 ratio, i.e., 2:1 rate block.

DESCRIPTION OF THE PREFERRED EMBODIMENT

The basic concept of this invention one of a single chamber pacemaker (AAD or VDD), where a sensed signal is either inhibited or triggered depending upon its time relationship to the last event. Thus, assuming a refractory interval, the pacemaker schedules an inhibit range (interval) which follows the refractory interval in time. Following the end of the inhibit range there is a scheduled trigger range (interval), the trigger range ending at the scheduled time out of the normal escape interval. Any sensed signal, noise or natural heartbeat, during the inhibit range results in the pacemaker not delivering a pace pulse, but extending the escape interval to a value longer than the normal scheduled escape interval. After such an inhibit event and extension of the escape interval, the pacer is then in a trigger mode until time out of the longer escape interval, during which time any sensed event results in delivery of a trigger pulse and resetting of the escape interval. If there is no sensed event during the inhibit range but one does occur during the trigger range, the pacemaker delivers a trigger pulse and resets to start the next time out of the scheduled escape interval.

Figure 1A:
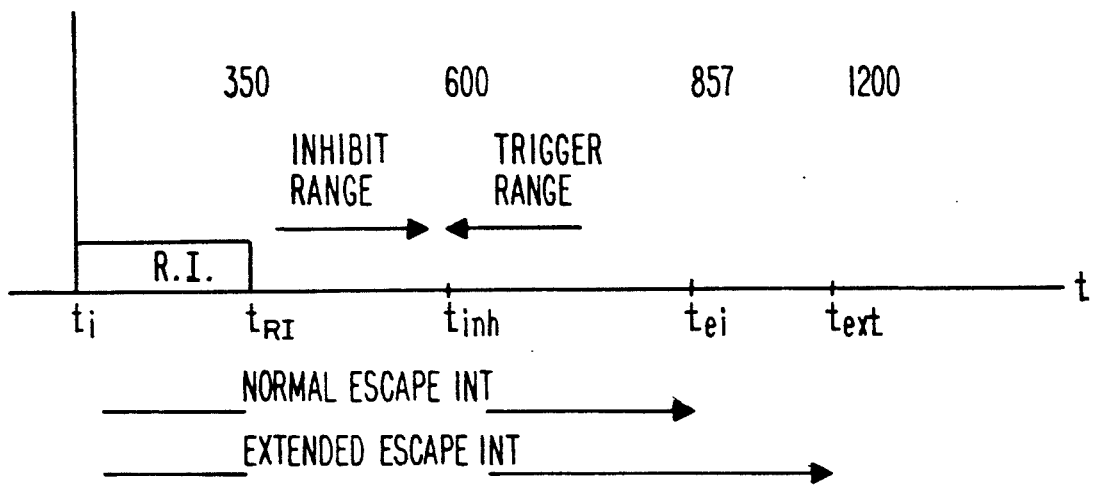
FIG. 1A is a timing diagram illustrating the inhibit and trigger ranges as defined for use in this invention, as well as the extended escape interval which is utilized following an inhibit event.

Referring now to FIG. 1A, there is presented a timing diagram illustrating the refractory interval, inhibit range and trigger range as discussed above. In this diagram, $t_1$ = the last event, i.e., either a trigger on a sensed signal or a time out of the normal or extended escape interval. The refractory interval commences at t and extends to $t_{RI}$. The refractory interval is nominally 300–350 ms, and is illustrated as 350 ms. The inhibit range follows the last event, but only after time out of a refractory interval. Thus, in the preferred embodiment, the inhibit range extends from $t_{RI}$ to $t_{inh}$. The trigger range extends from $t_{inh}$ to the time of the normally scheduled escape interval, $t_{ei}$. The extended escape interval, which is set upon the detection of an event in the inhibit range, is illustrated as $t_{ext}$. Nominally, the extended escape interval may be twice the time of the end of the inhibit range, i.e., $2 \times t_{inh}$. Thus, for an inhibit range that ends at 600 ms, the extended escape interval may be set at 1200 ms. The result of this arrangement is that for natural steady rates higher than the trigger range, every other beat is triggered, resulting in 2:1 block. This arrangement provides that there is a trigger for any beat falling within the trigger range, or any sensed event following an inhibited sensed event. The pacemaker cycle is never restarted at the time of an inhibition, but restarts only upon a delivery of a trigger pulse or delivery of a pace pulse following time out of the normal or extended escape interval.

Figure 1B:
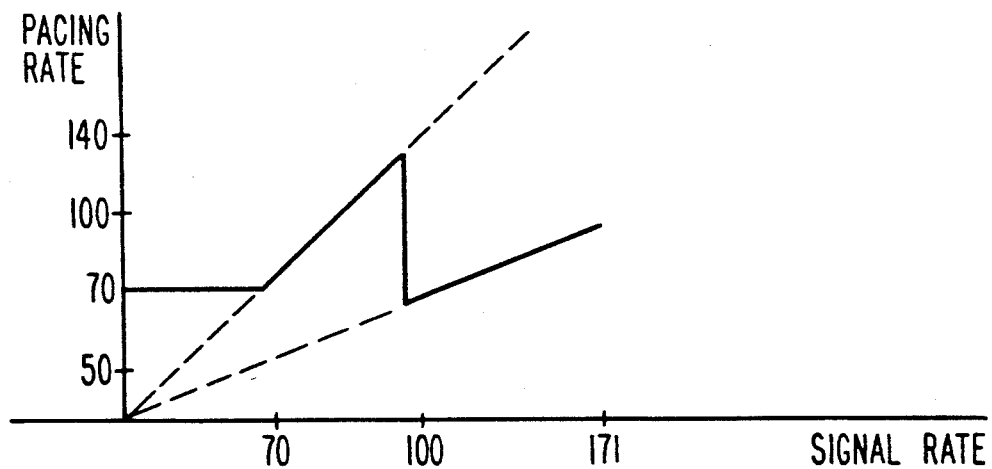
FIG. 1B is a rate diagram illustrating the pacing rate in response to sensed signal rate in accordance with this invention.

Referring to FIG. 1B, the rate diagram illustrates the response of the pacemaker in accordance with this invention. Any steady underlying rate which is less than that which corresponds to $t_{ei}$ results in a programmed pacing rate, e.g., 70 bpm. In the illustration of FIG. 1B, $t_{ei}$ is 857 ms, corresponding to a rate of 70 bpm; $t_{inh}$ is 600 ms, corresponding to a rate of 100 bpm; $t_{RI}$ is 350 ms, corresponding to a maximum rate of 140 bpm; and $t_{ext}$ is 1200 ms. Further, as discussed hereinbelow, the pacemaker may be rate responsive, in which case $t°$ may be a variable.

Figure 2:
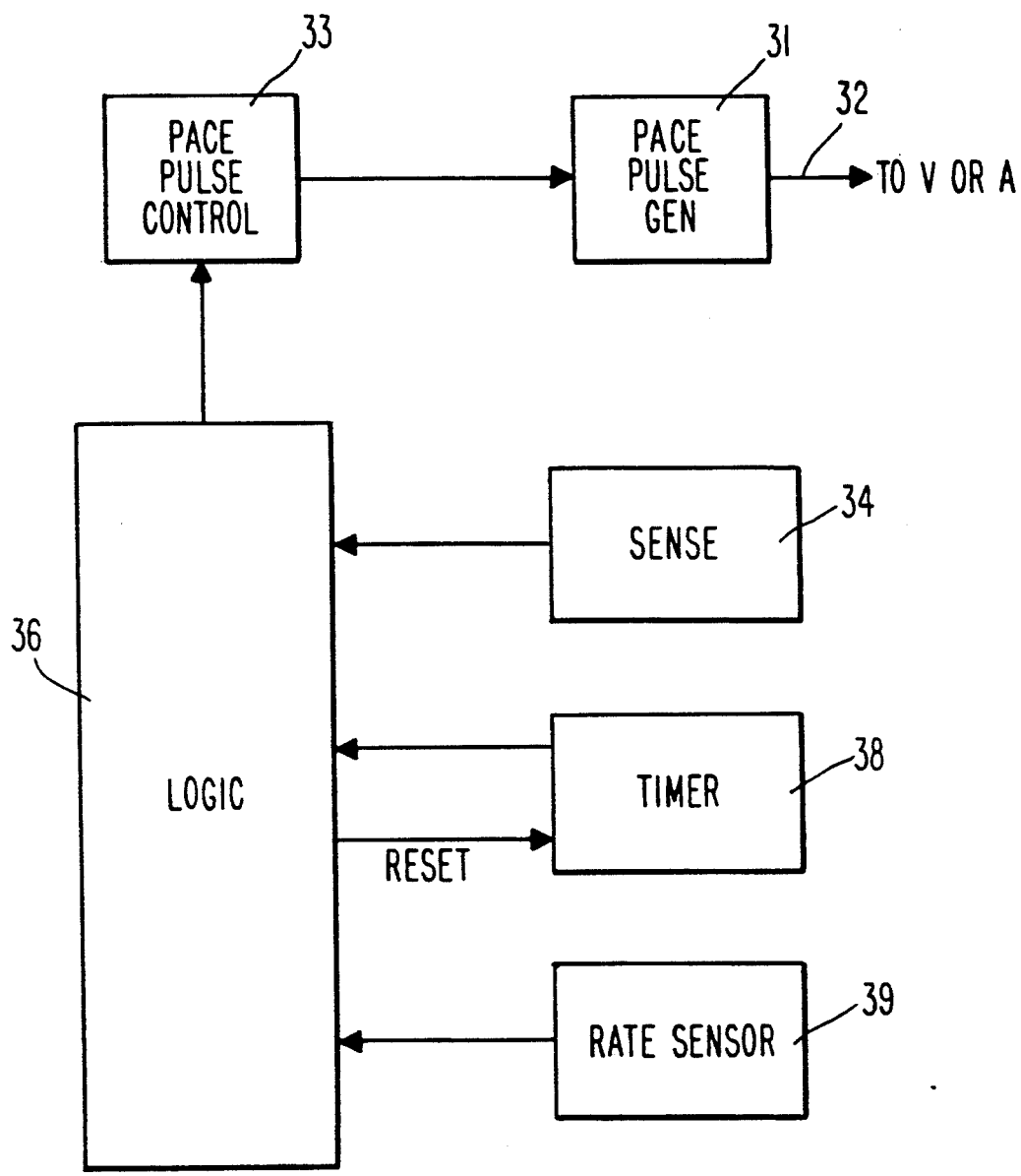
FIG. 2 is a block diagram showing the primary components of a pacemaker in accordance with this invention.

Referring now to FIG. 2, there is shown a block diagram of the primary components of a pacemaker in accordance with this invention. A pace pulse generator 31 generates pace pulses when triggered to do so, which pace pulses are connected by a lead 32 to the heart chamber, either ventricle or atrium. The pulse generator is controlled by pace pulse control circuit 33, which generates the timing pulse which is connected to generator 31 for determining time of initiation of the pulse and pulse width. Information concerning the amplitude may also be connected to generator 31. A sense circuit 34 is connected to receive signals picked up from the heart chamber by lead 32. The output of sense circuit 34 is connected to logic circuit 36, for processing and determining the next logical step of the pacemaker. Logic circuit 36 may be of any conventional form as is well known in the art, and suitably comprises a microprocessor and associated memory for holding desired software. A timer 38 is provided, under control of logic unit 36, for timing out intervals, as required. A rate sensor 39, of any suitable known form or forms, is utilized to derive one or more signals which are processed in unit 36 to derive an indicated pacing rate, in a well known fashion.

Figure 3:
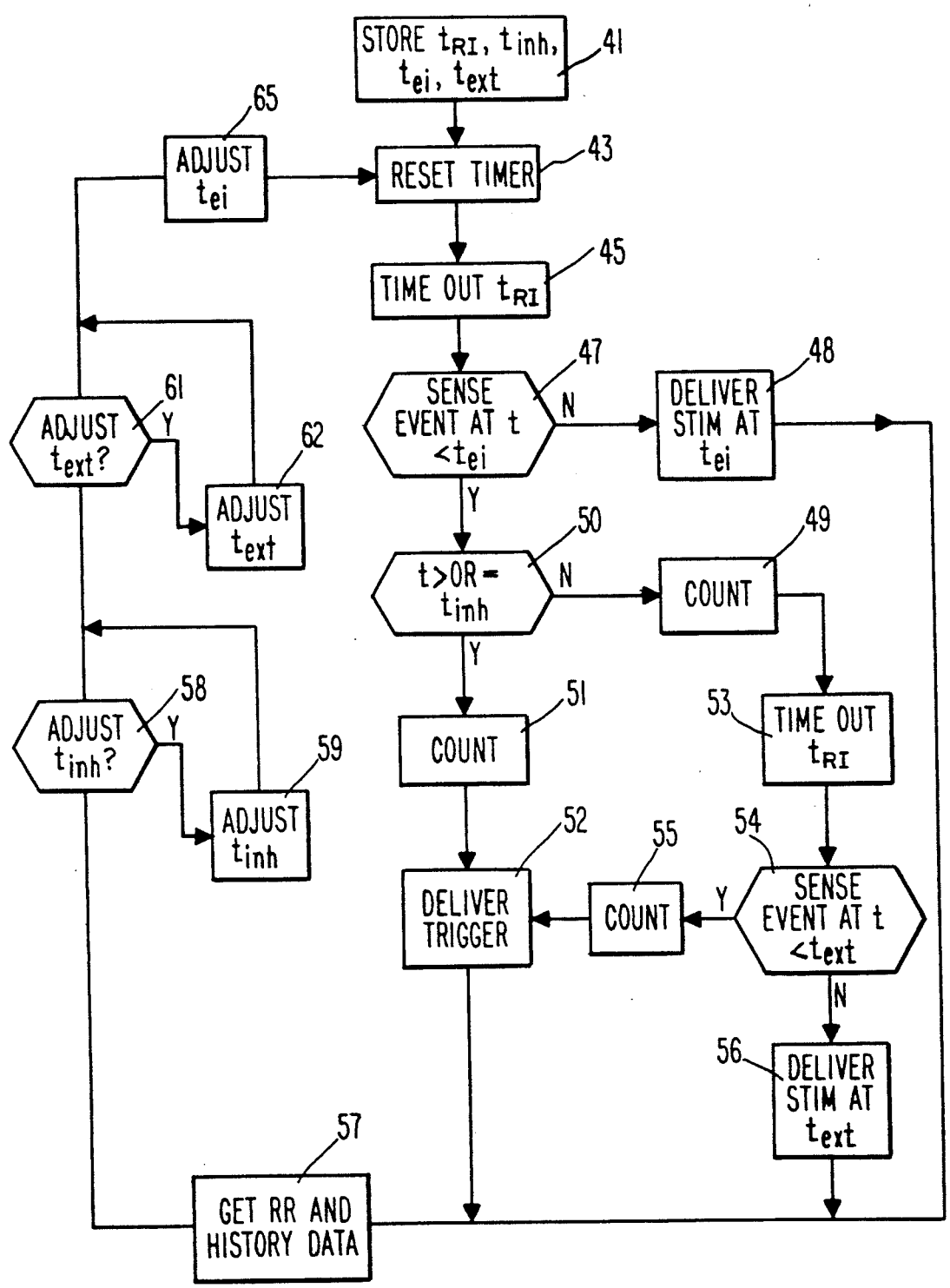
FIG. 3 is a logic diagram illustrating the sequence of logic steps for carrying out the method of this invention in a pacemaker.

Referring now to FIG. 3, there is shown a flow diagram, preferably carried out by software, for the pacemaker of this invention. The program is initialized at 41, including storage of the times as shown in FIG. 1A, e.g, $t_{RI}$, $t_{inh}$, $t_{ei}$, and $t_{ext}$. At block 43, the timer is reset, i.e., the pacemaker cycle is initiated. Following time out of the refractory interval at 45, the pacemaker waits until it either senses an event at $t < t_{ei}$, or determines that $t_{ei}$ has timed out, as illustrated at 47. If the escape interval $t_{ei}$ has timed out, the pacemaker delivers a pace pulse, as indicated at block 48. If an event has been sensed before time out, i.e., at $t < t_{ei}$, then the software proceeds to block 50 to determine whether the event has occurred within the inhibit interval, i.e., is t equal to or greater than $t_{inh}$? If t is not equal to or greater than $t_{inh}$, this means the signal has occurred in the inhibit range. The program branches to block 49 and counts the event, and then goes to block 53 and starts time out of another refractory interval. This is done to guard against a condition of repetitive noise at short intervals, which could result in a very early trigger pulse. After this, the program goes to block 54, where it waits to see if an event is sensed before the time out of $t_{ext}$, i.e., at $t < t_{ext}$. If such an event is sensed, the program branches to block 55 and counts, and then goes to block 52 where a trigger pace pulse is delivered. If there is no sensed event until the time out of $t_{ext}$, the program proceeds from 54 to 56, and a stimulus is delivered at time out of $t_{ext}$. Going back to block 50, if the event is sensed after $t_{inh}$, it is during the trigger range. The pacemaker goes to block 51 and counts, and then delivers a trigger pace pulse at block 52.

Following delivery of a pace pulse, either at block 48, 52 or 56, the program proceeds to block 57, where sensor and history data are retrieved. History data may be accumulated, e.g., by counting senses occurring in the inhibit range (block 49), senses occurring in the trigger range (block 51) and trigger events following an inhibit sense (block 55). At block 58 it is determined whether $t_{inh}$ is to be adjusted. In the practice of this invention, $t_{inh}$ may be adjusted under different circumstances. Thus, if a percentage of the n last senses (e.g., history data) are in the trigger range, indicating probability of a natural rate not too much above the rate corresponding to $t_{ei}$; or if the sensor data indicates a rate just above the programmed rate, $t_{inh}$ may be changed accordingly. If so, $t_{inh}$ is adjusted at block 59. At block 61, a similar determination based upon patient history and/or sensor data is made as to whether $t_{ext}$ should be adjusted, e.g., to maintain $t_{ext}$ at about $2 \times t_{inh}$. If such an adjustment is to be made, it is done at block 62. Before returning to block 43 and initiating a new cycle, the pacemaker may optionally adjust $t_{ei}$, as indicated at block 65. Thus, in a rate responsive pacemaker, $t_{ei}$ is suitably adjusted each pacing cycle, in a well known manner, in accordance with sensor information. Further, $t_{RI}$ may be varied in accordance with history or sensor data.

The history information can be used to let the pacer respond in a flywheel or overdrive mode. However, in a preferred embodiment, it can be used to determine if sensed signals are probably cardiac signals, or noise, and to adapt the inhibit and trigger ranges accordingly. If sensed signals are determined to be physiologic, $t_{inh}$ is shifted toward $t_{ei}$, so that the pacer functions primarily in the VVI (or AAI) mode. On the other hand, signals determined to be noise, or non-physiologic, result in $t_{inh}$ being shifted toward $t_{ei}$. The history data can be used to switch between strictly VVT (or AAT) ($t_{inh}=t_{RI}$) and VVI (or AAI) ($t_{inh}=t_{ei}$), or to maintain the VVD (or AAD) mode with varying inhibit and trigger ranges. In one embodiment, the pacer is normally in VVI mode, but is switched to VVD when the history data indicates continual existence of non-physiological heartbeat signals. Thus, the analysis at block 58 may include a determination of whether the last sensed event is physiological or non-physiological, as set forth in U.S. application Ser. No. 831,115, of the assignee of this application, incorporated by reference.

Reviewing the performance of the pacemaker of this invention, it is noted that triggering in response to natural beats has no adverse effect on pacemaker performance, except that the trigger pulses utilize battery energy which would not be utilized in the event of inhibition. However, the inhibit range works to reduce the number of trigger pulses that would otherwise be delivered at high natural rates in a VVT or AAT pacemaker. Further improvement comes in any situation where noise is present. In the presence of noise or other signal artifacts, the pacemaker of this invention ensures a pace reasonably properly timed at every event. The trigger pulse is delivered a little sooner in the presence of noise if it occurs within the trigger range, and a bit later if it occurs in the inhibit range. If the pacemaker is additionally rate responsive, the trigger range may be simply shortened when the sensor increases pacing rate (and shortens $t_{ei}$).

It is to be understood that the invention as described may be practiced in various equivalent ways. For example, instead of storing a time $t_{ext}$, the pacemaker may add predetermined interval $\Delta$ to $t_{ei}$, such that $t_{ei} = t_{ei} + \Delta$ after sensing a signal in the inhibit range. Other variations of the sequence of operations for carrying out the logic of the inhibit/trigger arrangement are within the scope of the claimed invention.

What is claimed:

1. A pacemaker for pacing at least one chamber of a patient's heart, having a pace generator for generating pace pulses, sense means for sensing signals from said chamber, and control means for normally timing out a normal escape interval following a last event for timing the generation of a pace pulse, comprising:
    inhibit means for defining a scheduled inhibit time range, and including response means for responding to a first sensed event within said inhibit time range by extending said escape interval to a longer interval, and
    trigger means for defining a scheduled trigger time range between said inhibit range and the end of said normal escape interval, said trigger means further having means for controlling said pace generator to generate a trigger pulse at the time of any signal sensed during said trigger range.

2. The pacemaker as described in claim 1, wherein said trigger means further comprises means for controlling said pace generator to generate a trigger pulse at the time of any signal sensed following a said first sensed event and before time out of said longer interval.

3. The pacemaker as described in claim 2, wherein said inhibit means comprises means for scheduling the end of said inhibit range at a first predetermined time interval following the last sense or pace event, and means for setting said extended escape interval to end at a time following said last event which is about two times the scheduled end of said inhibit range.

4. The pacemaker as described in claim 3, further comprising means for initiating a refractory interval substantially at the time of said last event, and wherein said inhibit means comprises means for initiating said inhibit time range at the end of said refractory interval.

5. The pacemaker as described in claim 4, further comprising means for timing out another refractory interval following sensing of a signal during said inhibit time range, and means for preventing response to a signal from said chamber during said another refractory interval.

6. The pacemaker as described in claim 1, further comprising a sensor means for developing a signal representative of desired pacing rate for said patient, and rate responsive control means further varying said normal escape interval as a function of said sensor signal.

7. The pacemaker as described in claim 1, further comprising a sensor means for developing a signal representative of desired pacing rate for said patient, and rate responsive control means further varying any one of (a) said normal escape interval, (b) said extended escape interval, (c) said inhibit range, and (d) said trigger range, as a function of said sensor signal.

8. The pacemaker as described in claim 1, comprising data means for acquiring data representative of sensed events, and adjust means for adjusting at least one of said inhibit range and said trigger range as a function of said acquired data.

9. A single chamber pacemaker, comprising sensing means for sensing signals from a chamber of a patient's heart, pace pulse generator means for generating and delivering pace pulses to said patient chamber, trigger mode means for placing said pacemaker in a trigger mode, thereby controlling said generator means to deliver a trigger pulse when said sensing means senses a signal,
    first timing means for timing a normal escape interval,
    second timing means for timing a refractory interval,
    third timing means for timing an inhibit interval,
    fourth timing means for timing a trigger interval which follows said inhibit interval and has a scheduled end coincident with the end of said normal escape interval,
    firth timing means for timing an extended escape interval,
    inhibit means for responding to a signal sensed during said inhibit interval, by controlling said trigger mode means to place said pacemaker into said trigger mode for the remaining duration of said extended interval; and
    trigger means for controlling said trigger mode means to place said pacemaker into said trigger mode during said trigger interval.

10. A pacemaker for pacing at least one chamber of a patient's heart, having pace pulse generator means for generating pace pulses, sense means for sensing signals from said chamber, and control means for normally timing out a normal escape interval following a last event for timing the generation of a pace pulse, said control means further characterized by:
    inhibit range means for timing out an inhibit range following a generated pulse;
    trigger range means for timing out a trigger range following said inhibit range;
    first determining means for determining when a said sensed signal is in said inhibit range and second determining means for determining when a said sensed signal is in said trigger range;
    trigger mode means for placing said pacemaker in a trigger mode and thereby controlling said generator means to deliver a trigger pulse when said sensing means senses a signal,
    first response means for responding to a sensed signal determined to be in said inhibit range by extending said escape interval without delivery of a pace pulse, and controlling said trigger mode means to place said pacemaker in said trigger mode for at least a portion of the remaining time until time out of the extended escape interval; and
    second means for controlling said trigger mode means to place said pacemaker in said trigger mode during said trigger range.

11. The pacemaker as described in claim 10, comprising data means for collecting history data representative of sensed events, and means for adjusting said inhibit range and said trigger range in accordance with said history data.

12. The pacemaker as described in claim 11, further comprising mode means to place said pacemaker into one of VVI and AAI modes of operation.

13. The pacemaker as described in claim 11, further comprising mode means to place said pacemaker into one of VVT and AAT modes of operation.

14. A pacemaker for pacing at least one chamber of a patient's heart, having pace pulse generator means for generating pace pulses, sense means for sensing signals from said chamber, and control means for normally timing out a normal escape interval following a last event for timing the generation of a pace pulse, said control means further characterized by history data means for characterizing the events corresponding to said sensed signals and storing data representative thereof, said control means comprising inhibit mode means for controlling said pacemaker in an inhibit mode and trigger mode means for controlling said pacemaker in a trigger mode, said control means further having data analysis means for controlling said pacemaker in at least one of said inhibit and trigger modes as a function of said data.

15. The pacemaker as described in claim 14, wherein said data analysis means comprises first means for normally controlling said pacemaker to be in said inhibit mode, and second means for controlling said pacemaker to be in said trigger mode as a function of said data.

16. The pacemaker as described in claim 15, wherein said data analysis means comprises third means for controlling said pacemaker to be in a combined inhibit and trigger mode as a function of said data.

17. A pacemaker for pacing at least one chamber of a patient's heart, having a pulse generator for generating and delivering pulses to said patient's heart, sense means for sensing signals from said patient's heart, control means for controlling the timing of said generated and delivered pulses, said control means having normal escape interval means for timing out a normal escape interval following a last pulse or sense event, and control means further comprising:

means operative after each said delivered pulse for timing out an inhibit time period, and first response means for responding to a first sensed event within said inhibit time period by timing out an extended escape interval, and trigger means for timing out a trigger time range between said inhibit range and the end of said normal escape interval, and trigger response means for controlling said pulse generator to generate and deliver a pulse at the time of any signal sensed by said sensing means during said trigger range and during said extended escape interval following a said first sensed event.

* * * * *

UNITED STATES PATENT AND TRADEMARK OFFICE
CERTIFICATE OF CORRECTION

PATENT NO. : 5,312,447
DATED : May 17, 1994
INVENTOR(S) : Malcolm J.S. Begemann

It is certified that error appears in the above-indentified patent and that said Letters Patent is hereby corrected as shown below:

At column 3, line 30, "$t^o$" should read --$t_{ei}$--

At column 4, line 55, "$t_{ei}$" should read --$t_{RI}$--

Signed and Sealed this

Sixteenth Day of August, 1994

Attest:

BRUCE LEHMAN

Attesting Officer        Commissioner of Patents and Trademarks